US007033026B2

(12) United States Patent
Spector (10) Patent No.: US 7,033,026 B2
(45) Date of Patent: *Apr. 25, 2006

(54) METHOD OF AND APPARATUS FOR DIAGNOSING AND TREATING AMBLYOPIC CONDITIONS IN THE HUMAN VISUAL SYSTEM

(76) Inventor: Robert T. Spector, 60 Lincoln St., New Haven, CT (US) 06511

( * ) Notice: Subject to any disclaimer, the term of this patent is extended or adjusted under 35 U.S.C. 154(b) by 0 days.

This patent is subject to a terminal disclaimer.

(21) Appl. No.: 10/613,987

(22) Filed: Jul. 4, 2003

(65) Prior Publication Data

US 2005/0001980 A1    Jan. 6, 2005

(51) Int. Cl.
*A61B 3/00* (2006.01)

(52) U.S. Cl. ..................................... 351/246
(58) Field of Classification Search ............... 351/200, 351/201, 203, 205, 216, 219, 246
See application file for complete search history.

(56) References Cited

U.S. PATENT DOCUMENTS

| | | | |
|---|---|---|---|
| 3,027,803 A * | 4/1962 | Filderman | 351/160 R |
| 4,057,054 A | 11/1977 | Giannone | |
| 4,134,401 A | 1/1979 | Galician | |
| 4,726,672 A | 2/1988 | O'Brien et al. | |
| 4,896,959 A | 1/1990 | O'Brien | |
| 4,979,812 A * | 12/1990 | Reese | 351/246 |
| 5,956,126 A * | 9/1999 | Cody | 351/246 |
| 6,149,615 A | 11/2000 | Gallamore | |
| 6,273,092 B1 | 8/2001 | Nolan | |
| 6,511,175 B1 * | 1/2003 | Hay et al. | 351/45 |
| 6,540,900 B1 | 4/2003 | Kinard et al. | |
| 2003/0208265 A1 * | 11/2003 | Ho et al. | 623/4.1 |
| 2003/0214630 A1 * | 11/2003 | Winterbotham | 351/203 |

OTHER PUBLICATIONS

Marr, D., Vision: A Computation Investigation into the Human Representation and Processing of Visual Information, 1982, pp. viii, ix, 111-161, W.H. Freeman and Company, New York.
Search Report for International Application No. PCT/US04/21590.

* cited by examiner

*Primary Examiner*—Brian L. Casler
*Assistant Examiner*—John R Sanders
(74) *Attorney, Agent, or Firm*—Thomas J. Perkowski, Esq., P.C.

(57) ABSTRACT

A method of and apparatus for diagnosing and treating amblyoptic conditions within the human vision system, wherein optical magnification is used to provide an amblyopic eye with more photonic energy than the non-amblyopic eye during treatment so as to over-stimulate the neural pathways along the visual channel of the amblyopic eye, and eventually achieve harmony along the both visual channels of the patient over the course of treatment, without the use of occlusion therapy.

6 Claims, 13 Drawing Sheets

Visual Channel Equalization in Human Vision System:
Case: Single Eye Correction

The Human Eye

Visual Channel Equalization in Human Vision System:
Case: Single Eye Correction

METHOD OF AND APPARATUS FOR DIAGNOSING AND TREATING AMBLYOPIC CONDITIONS IN THE HUMAN VISUAL SYSTEM

BACKGROUND OF INVENTION

1. Field of Invention

The present invention relates to an improved method of, and apparatus for, diagnosing and treating amblyopic conditions in the visual system of human patients, in a safe, effective and inexpensive manner.

2. Brief Description of the State of Knowledge in the Art in the Field of Invention Currently, a great deal has been written about the vision-related problem referred to as "amblyopia" which afflicts millions of individuals annually is the major cause of blindness throughout the world. Reference can be made to the following publications for conventional methods of detection and treatment for this condition:

American Academy of Ophthalmology: Amblyopia. Basic and Clinical Science Course: Pediatric Ophthalmology and Strabismus 1997; 259–265.

Daw N W: Critical periods and amblyopia. Arch Ophthalmol 1998 Apr; 116(4): 502–5;

Flynn J T: Amblyopia: its treatment today and its portent for the future. Binocul Vis Strabismus Q 2000 Summer; 15(2): 109;

Flynn J T, Woodruff G, Thompson J R, et al: The therapy of amblyopia: an analysis comparing the results of amblyopia therapy utilizing two pooled data sets. Trans Am Ophthalmol Soc 1999; 97: 373–90; discussion 390–5;

Flynn J T: 17th annual Frank Costenbader Lecture. Amblyopia revisited. J Pediatr Ophthalmol Strabismus 1991 July–August; 28(4): 183–201;

Kirschen D G: Understanding Sensory Evaluation. In: Rosenbaum A L and Santiago A P. Clinical Strabismus Management: Principles and Practice. 1999: 22–35;

Kushner, B J: Amblyopia. In: Nelson L B, ed. Harley's Pediatric Ophthalmology. 1998: 125–39; and von Noorden G K: Binocular Vision and Ocular Motility: Theory and Management. 1996: 216–54.

As taught by these medical references, amblyopia refers to a decrease of vision, either unilaterally or bilaterally, for which no cause can be found by physical examination of the eye. The term functional amblyopia often is used to describe amblyopia, which is potentially reversible by occlusion therapy. Organic amblyopia refers to irreversible amblyopia.

Most vision loss from amblyopia is preventable or reversible with the right kind of intervention. The recovery of vision depends on how mature the visual connections are, the length of deprivation, and at what age the therapy is begun. It is important to rule out any organic cause of decreased vision because many diseases may not be detectable on routine examination.

Although many types of amblyopia exist, it is believed that their basic Pathophysiological mechanisms are the same even though each factor may contribute different amounts to each specific type of amblyopia. In general, amblyopia is believed to result from disuse from inadequate foveal or peripheral retinal stimulation and/or abnormal binocular interaction that causes different visual input from the foveas.

Three critical periods of human visual acuity development have been determined. During these time periods, vision can be affected by the various mechanisms to cause or reverse amblyopia. These periods are as follows:

Development of visual acuity from the 20/200 range to 20/20, which occurs from birth to age 3–5 years;

Period of highest risk of deprivation amblyopia, from a few months to 7 or 8 years; and The period during which recovery from amblyopia can be obtained, from the time of deprivation up to teenage or even, sometimes, adult years.

Whether different visual functions (e.g, contrast sensitivity, stereopsis) have different critical periods is reported as not known in the scientific literture. It is said that in the future, determination of these time frames may help modify treatment of amblyopia.

In the US, the prevalence of amblyopia is difficult to assess and varies in the literatures ranging from 1.0–3.5% in healthy children to 4.0–5.3% in children with ophthalmic problems. Most data show that about 2% of the general population has amblyopia.

Amblyopia was shown in the Visual Acuity Impairment Survey sponsored by the National Eye Institute (NEI) to be the leading cause of monocular vision loss in adults aged 20–70 years or older. Prevalence of amblyopia has not changed much over the years.

Amblyopia is an important socioeconomic problem. Studies have shown that it is the number one cause of monocular vision loss in adults. Furthermore, amblyopes have a higher risk of becoming blind because of potential loss to the sound eye from other causes.

Amblyopia occurs during the critical periods of visual development. An increased risk exists in those children who are developmentally delayed, were premature, and/or have a positive family history.

Diagnosis of amblyopia usually requires a 2-line difference of visual acuity between the eyes; however, this definition is somewhat arbitrary and a smaller difference is common.

A common characteristic of amblyopic eyes is difficulty in distinguishing optotypes that are close together. Visual acuity often is better when the patient is presented with single letters rather than a line of letters. Diagnosis is not an issue in children old enough to read or with use of the "tumbling E."

If the child protests with covering of the sound eye, amblyopia can be diagnosed if it is dense.

Fixation preference may be assessed, especially when strabismus is present.

Induced tropia test may be performed by holding a 10-prism diopter before one eye in cases of an orthophoria or a microtropia.

In infants who cross-fixate, attention should be paid to when the fixation switch occurs; if it occurs near primary position, then visual acuity is equal in both eyes.

Caution should be used when obtaining Teller acuity in children, as grating acuity may be less reduced than Snellen acuity, especially in strabismic amblyopia.

Strabismic and anisometropic amblyopic eyes have marked losses of threshold contrast sensitivity, especially at higher spatial frequencies; this loss increases with the severity of amblyopia.

Patients with strabismic amblyopia may have better visual acuity or less of a decline of visual acuity when tested with neutral density filters compared to the normal eye. This was not found to be true in patients with anisometropic amblyopia or organic disease.

Amblyopia usually is associated with changes in binocular function or stereopsis.

Some amblyopes may consistently fixate with a nonfoveal area of the retina under monocular use of the amblyopic eye, the mechanism of which is unknown. This can be diagnosed by holding a fixation light in the midline in front of the patient and asking them to fixate on it while the normal eye is covered. The reflection of the light will not be centered.

Cycloplegic refraction must be performed on all patients, using retinoscopy to obtain an objective refraction. In most cases, the more hyperopic eye or the eye with more astigmatism will be the amblyopic eye. If this is not true, one needs to investigate further for ocular pathology.

A full eye examination should be performed to rule out ocular pathology.

While many causes of amblyopia exist, the most important are as follows: Anisometropia; Strabismus; Strabismic anisometropia; Visual deprivation and Organic abnormalities.

In the case of Anisometrop, inhibition of the fovea occurs to eliminate the abnormal binocular interaction caused by one defocused image and one focused image. This type of amblyopia is more common in patients with anisohypermetropia than anisomyopia. Small amounts of hyperopic anisometropia, such as 1–2 diopters, can induce amblyopia. In myopia, mild myopic anisometropia up to –3 diopters usually does not cause amblyopia. Hypermetropic anisometropia of 1.50 diopters or greater is a long-term risk factor for deterioration of visual acuity after occlusion therapy.

In the case of Strabismus, the patient favors fixation strongly with one eye and does not alternate fixation. This leads to inhibition of visual input to the retinocortical pathways. Incidence of amblyopia is greater in esotropic patients than in exotropic patients.

In the case of Strabismic anisometropia, patients have strabismus associated with anisometropia In the case of visual deprivation, amblyopia results from disuse or understimulation of the retina. This condition may be unilateral or bilateral. Examples include cataract, corneal opacities, ptosis, and surgical lid closure.

In the case of organic abnormalities, structural abnormalities of retina or optic nerve may be present. Functional amblyopia may be superimposed on the organic visual loss.

If suspicion exists of an organic cause for decreased vision and the ocular examination is normal, then further investigations into retinal or optic nerve causes should be initiated. Studies to perform include imaging of the visual system through CT scan, MRI, and fluorescein angiography to assess the retina.

Although differences in the electrophysiologic responses of normal versus amblyopic eyes have been reported, these techniques remain investigational and the differences are controversial.

The conventional course of medical care for amblyopic patients is as follows:

The clinician must first rule out an organic cause and treat any obstacle to vision (eg, cataract, occlusion of the eye from other etiologies).

Remove cataracts in the first 2 months of life, and aphakic correction must occur quickly.

Treatment of anisometropia and refractive errors must occur next.

The amblyopic eye must have the most accurate optical correction possible. This should occur prior to any occlusion therapy because vision may improve with spectacles alone.

Full cycloplegic refraction should be given to patients with accommodative esotropia and amblyopia. In other patients, a prescription less than the full plus measurement that was refracted may be prescribed given that the decrease in plus is symmetric between the two eyes. Because accommodative amplitude is believed to be decreased in amblyopic eyes, one needs to be cautious about cutting back too much on the amount of plus.

The next step is forcing the use of the amblyopic eye by occlusion therapy. Occlusion therapy has been the mainstay of treatment since the 18th century.

The following are general guidelines for occlusion therapy:

Patching may be full-time or part-time. In general, children need to be observed at intervals of 1 week per year of age, if undergoing full-time occlusion to avoid occlusion amblyopia in the sound eye.

Always consider lack of compliance in a child where visual acuity is not improving. Compliance is difficult to measure but is an important factor in determining the success of this therapy.

In addition to adhesive patches, opaque contact lenses, occluders mounted on spectacles, and adhesive tape on glasses have been used.

Establishing the fact that the vision of the better eye has been degraded sufficiently with the chosen therapy is important.

For children who will not wear a patch or in whom compliance is an issue, penalization therapy can be used. The following are general guidelines for penalization therapy:

Atropine drops or ointment is instilled in the nonamblyopic eye. This therapy may be (and is preferably) used in conjunction with patching or occlusion of the glasses (eg, adhesive tape, nail polish).

This technique also may be used for maintenance therapy, which is useful especially in mild amblyopes.

Currently, the Amblyopia Treatment Study is ongoing to determine whether the success rate with atropine treatment of amblyopia as a primary treatment is equivalent to the success rate of occlusion therapy. The results of this study will be helpful in determining the exact role of atropine penalization in the treatment of amblyopia.

Other options include optical blurring through contact lenses or elevated bifocal segments.

The endpoint of therapy is spontaneous alternation of fixation or equal visual acuity in both eyes. When visual acuity is stable, patching may be decreased slowly, depending on the child's tendency for the amblyopia to recur. Because amblyopia recurs in a large number of patients, maintenance therapy or tapering of therapy should be strongly considered. This tapering is controversial, so individual physicians vary in their approaches.

Close supervision during occlusion therapy is necessary to make sure children do not peek. Various methods of preventing children from removing patches have been considered, from a reward system for older children to arm splints and mittens for infants.

Pharmacologic treatment with levodopa has been investigated and has showed transient improvement of vision in amblyopic eyes. However, the exact role of such pharmacologic agents has not been determined. Levodopa currently is not being used clinically.

Atropine penalization (with either ointment or drops) is an alternative method of blurring vision in the sound eye of patients who refuse patching. It may be applied once a day to patients in the preferred eye only.

Outpatient follow-up needs to continue beyond the primary completion of amblyopia treatment because visual deterioration occurs in many children. One study by Levartovsky et al showed deterioration in 75% of children with anisometropia of 1.75 diopters or more after occlusion therapy. Recidivism can occur even several years after the initial treatment period and is as high as 53% after 3 years.

The main complication of not treating amblyopia is long-term irreversible vision loss. Most cases of amblyopia are reversible if detected and treated early, so this vision loss is preventable. After 1 year, about 73% of patients show success after their first trial of occlusion therapy. Studies have shown that the number of patients who retain their level of visual acuity decreases over time to 53% after 3 years.

Risk factors for failure in amblyopia treatment include the following:

(1) the type of amblyopia, in which high anisometropes and patients with organic pathology have worse prognosis, and strabismic amblyopes have the best outcome.

(2) the age at which therapy began, in which younger patients seem to do better; and (3) the depth of amblyopia at the start of therapy, in which the better the initial visual acuity in the amblyopic eye, the better the prognosis.

While the current state of medical knowledge and practice recommends a great deal in the way of treatment based primarily on occlusion therapy, such methods and associated apparatus offer little, if any, hope of restoring full binocular vision to amblyopic patients.

Accordingly, there is a great need in the art for an improved method of and apparatus for diagnosing and treating amblyoptic conditions within the human vision system, while avoiding the shortcomings and drawbacks of prior art apparatus and methodologies.

SUMMARY AND OBJECTS OF INVENTION

Accordingly, it is an object of the present invention to provide an improved method of and apparatus for diagnosing and treating amblyoptic conditions within the human vision system, while avoiding the shortcomings and drawbacks of prior art apparatus and methodologies.

It is a further object of the present invention to provide such a method, wherein optical magnification is used to provide an amblyopic eye with more photonic energy than the non-amblyopic eye during treatment so as to overstimulate the neural pathways along the visual channel of the amblyopic eye, and eventually achieve harmony along the both visual channels of the patient over the course of treatment.

It is a further object of the present invention to provide such a method, wherein occlusion therapy is only used initially, at the earliest stage of treatment, when the depth of suppression has been determined to be very deep, and neural pathways need to be generated in the amblyopic visual channel rapidly while severely penalizing the non-amblyopic eye during this early stage of treatment.

It is a further object of the present invention to provide such a method, which can be used for cases of both monocular and binocular amblyopia.

Yet another object of the present invention is to provide apparatus in the form of an afocal binocular lens system applied before the amblyopic eye of a patient so as to treat monocular amblyopia by achieving harmony among the visual channels thereof using selective magnification along one visual channel according to the principles of the present invention.

Yet another object of the present invention is to provide apparatus in the form of a pair of reverse-afocal binocular lens systems applied before a pair of amblyopic eyes in a patient so as to treat binocular amblyopia by achieving harmony among the visual channels thereof using selective magnification along both visual channels according to the principles of the present invention.

Yet another object of the present invention is to provide apparatus in the form of workstation for carrying out the method of the present invention in clinical settings.

These and other objects of the present invention will become apparent hereinafter and in the Claims to Invention appended hereto.

DETAILED DESCRIPTION OF ILLUSTRATIVE EMBODIMENTS OF THE PRESENT INVENTION

The Detailed Description set forth below discloses a detailed specification of a novel method of treating amblyoptic conditions within the human vision system, and illustrative embodiments of apparatus for treating the same. These illustrative embodiments will now be described in detail with reference to the accompanying Drawings, wherein like structures and elements shown throughout the figures thereof shall be indicated with like reference numerals and/or characters.

Figure 1:
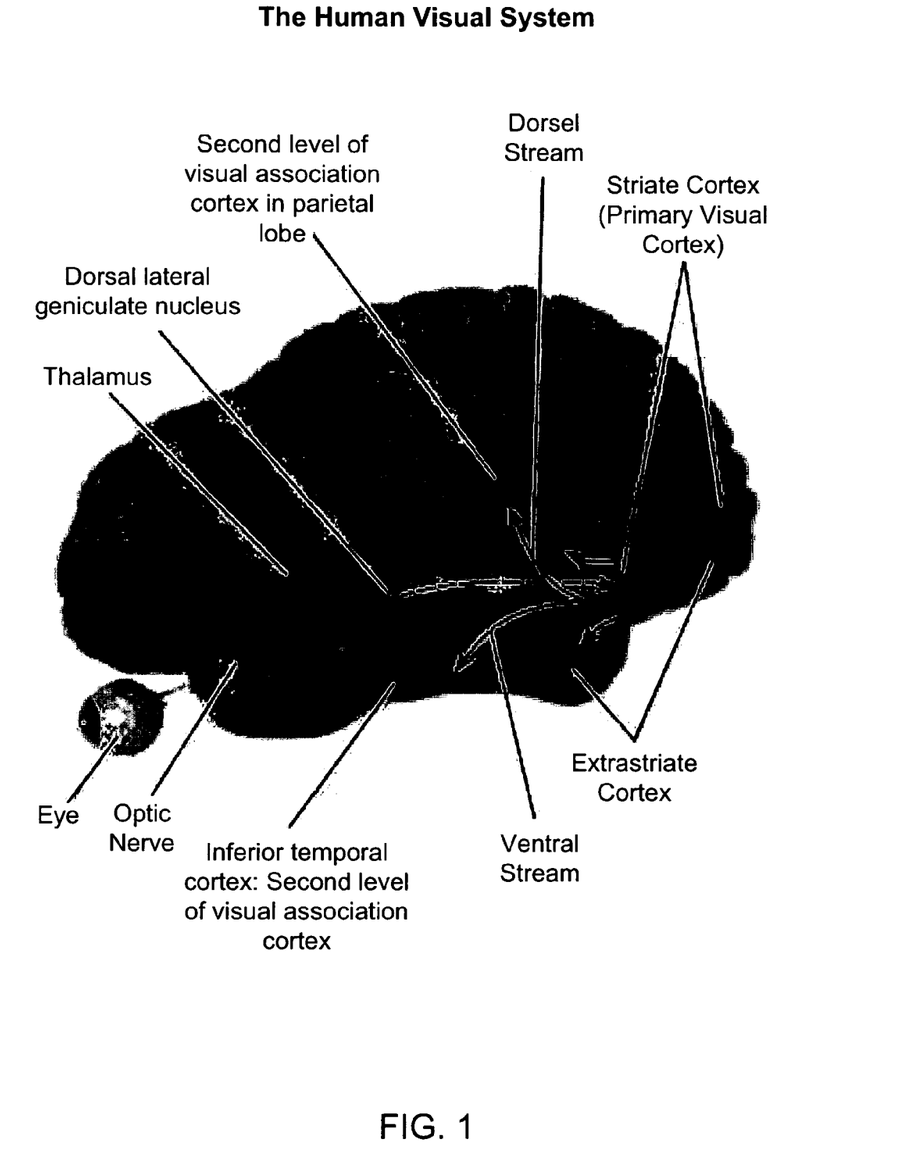
FIG. 1 is a graphical illustration of the human visual system, showing how the eyes, optical nervers are integrated with the corpus of the human brain in a fantastic manner.
Figure 2:
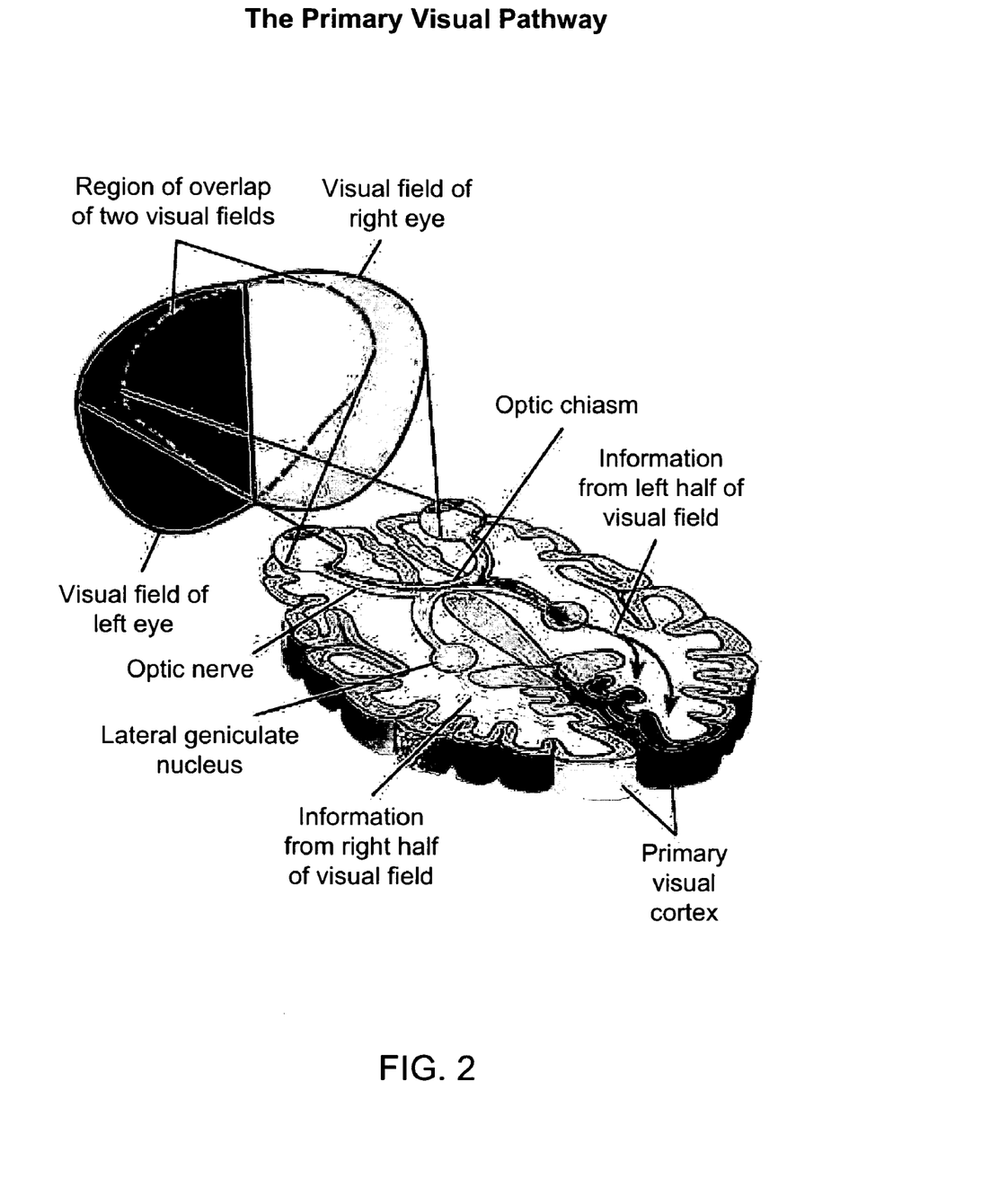
FIG. 2 is a schematic, cross-sectional illustration of the human visual system shown in FIG. 1, illustrating the primary visual pathway, in relation to the visual fields of the left and right eyes of the system.
Figure 3:
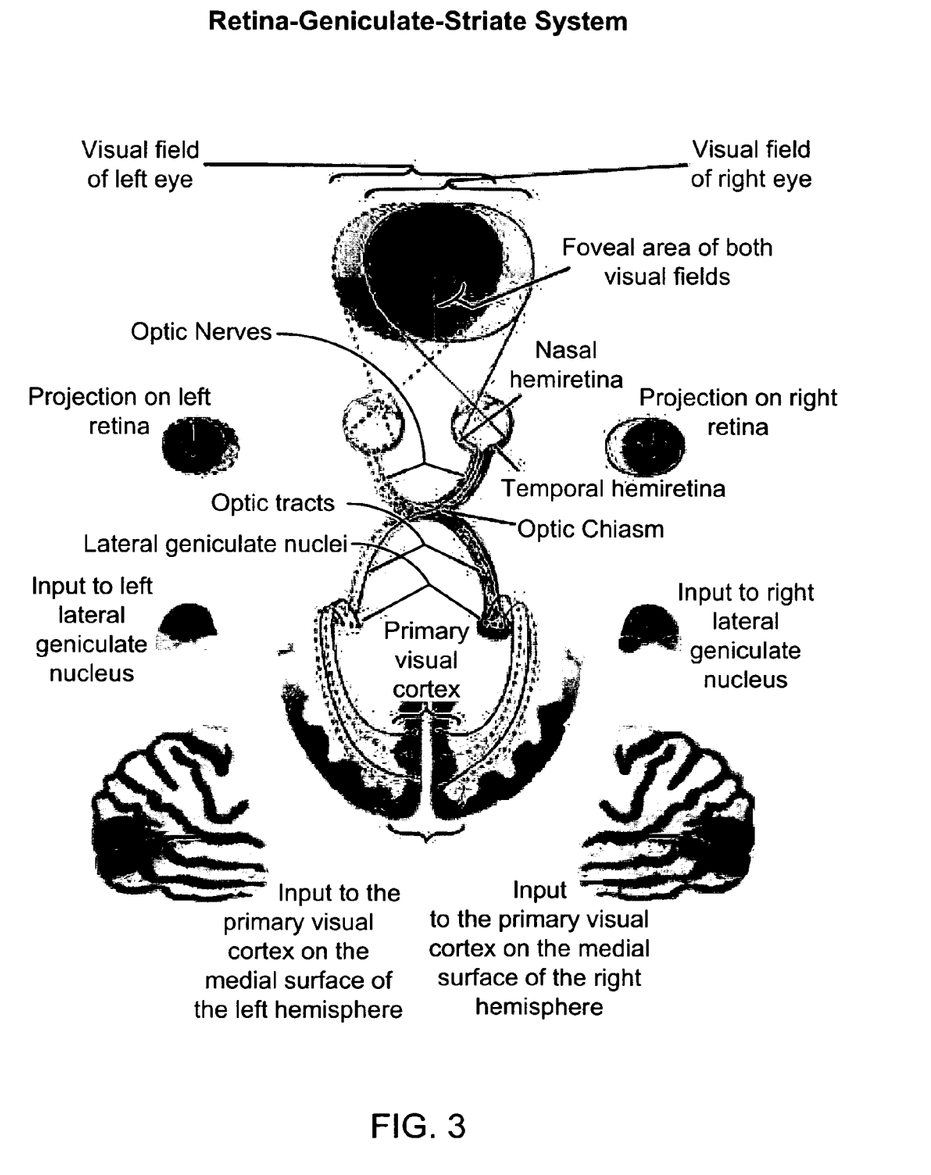
FIG. 3 is a schematic illustration of the retina-geniculate-striate system.
Figure 4:
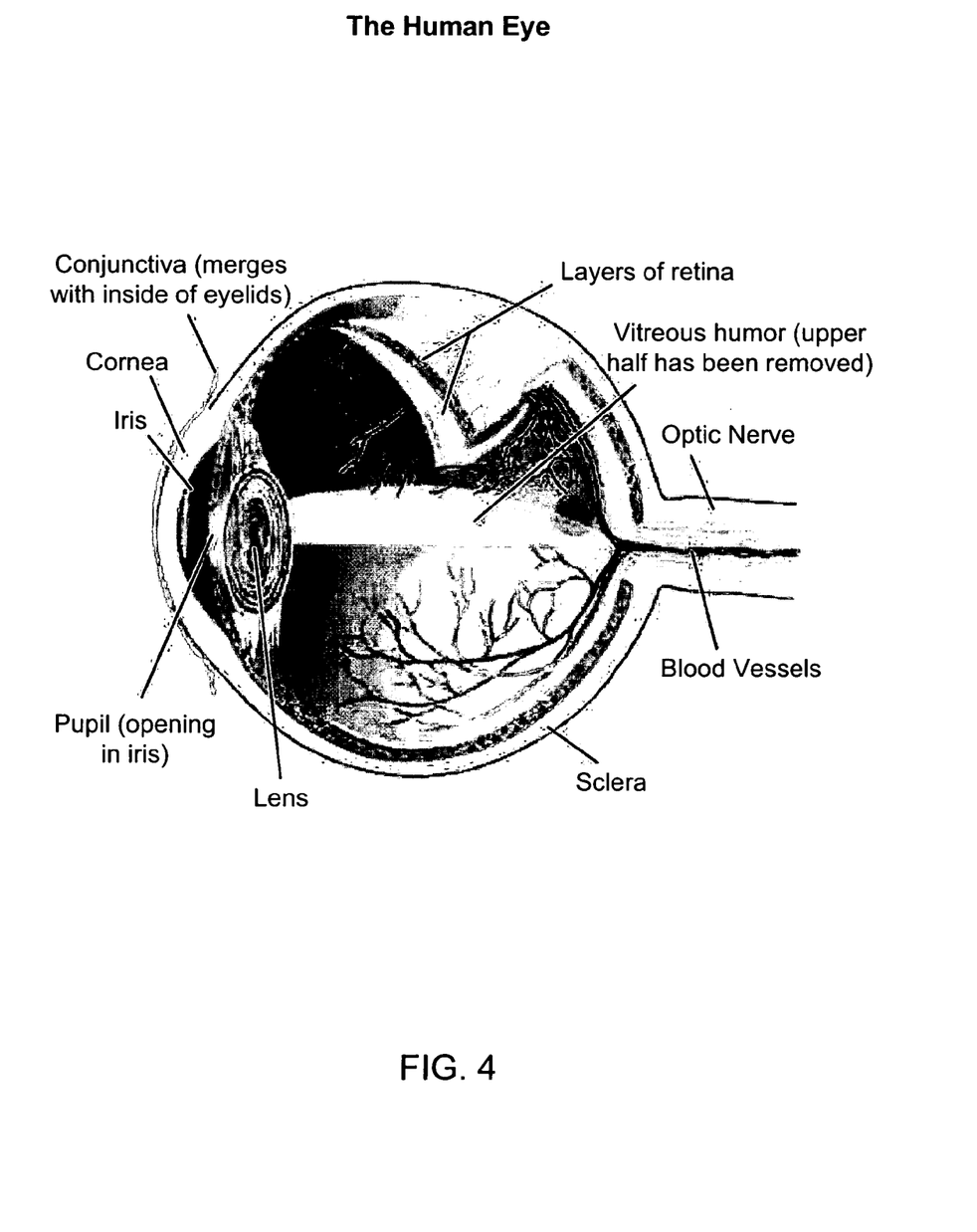
FIG. 4 is a schematic illustration of one eye in the human visual system.

In accordance with the principles of the present invention, the condition referred to as "amblyopia" covers a number of different entities resulting from impairments at different levels of the retino-cortical channels of the human visual system of a patient (hereinafter referred to as "subject")

shown in FIG. 1. The many forms of amblyopia are similar and can be identified as abnormal binocular interaction and foveal-cerbral deprivation, or a combination of both factors. These forms of affliction have one thing in common: visual stimuli in the visual pathway of the patient has been somehow suppressed for a prolonged duration (e.g. by faulty ocular accomodation and/or other optical dysfunction along the left and right visual channels), and as a result, sensory interference within the brain has been eliminated by virtue of the fact that left and right perspective images, originating from a fixation-focal point in the subject's field of view and formed via different image formation parameters (e.g. the left image is focused on the left retina while the right image is unfocused on the right retina) generate left and right retino-cortical signals which are superimposed within the visual cortex of brain. Expressed in other words, when left and right perspective images are formed on the retinas of a subject's left and right eyes, while having different image spot sizes and contours, retino-cortical signals are not generated and transmitted along corresponding retina-cortical pathways, and therefore corrresponding left and right images cannot achieve sensory fusion within the brain (i.e. cerebral sensory fusion), and binocular single vision cannot occur. This condition, understood by Applicant as amblyopia, is caused by there being a difference or disparity in the optical characteristics of a subject's left and right optical channels for a prolonged period of time (e.g. when the subject's retino-cortical channels are still developing), and severely effect the lives of children afflicted with this condition.

In accordance with the principles of the present invention, it is understood that for sensory fusion to occur within the brain, both the left and right perspective images originating from a fixation-focal point in the subject's field of view must not only be focused onto the subject's retinas and located in the corresponding retinal areas, but such left and right channel images must also be sufficiently similar in size, brightness, and sharpness to allow cerebral sensory fusion to occur, which can only be formed using image formation parameters that functionally produce isomorphic images in the left and right optical channels. In 1962, Hubel and Wiesal defined the process of cerebral sensory fusion, as being the "cerebral perception unification" of the images received in corresponding locations in two retinas of a human subject and channeled through the visual pathways to various locations in the brain.

The method of the present invention relies on Hubel and Wiesal's concept of "cerebral perception unification" and teaches a novel method of treating amblyopic conditions in the human vision system of a subject by optically conditioning the light associated with left and right images formed within the subject's field of view so that both left and right images are equally focused onto the same retinal areas of the subject's left and right eyes and have substantially same spot size and sharpness (i.e. image contrast). This optical correction process shall be referred to hereafter as "visual channel equalization" in that it seeks to compensate one or both visual channels in a subject so that both left and right channel signals are generated and transmitted (i.e. channeled) along corresponding retino-cortical pathways and undergo sensory fusion within the subject's brain.

In accordance with the present invention, a novel method is disclosed for diagnosing and treating amblyopic conditions in the visual system of a patient.

Figure 5A:
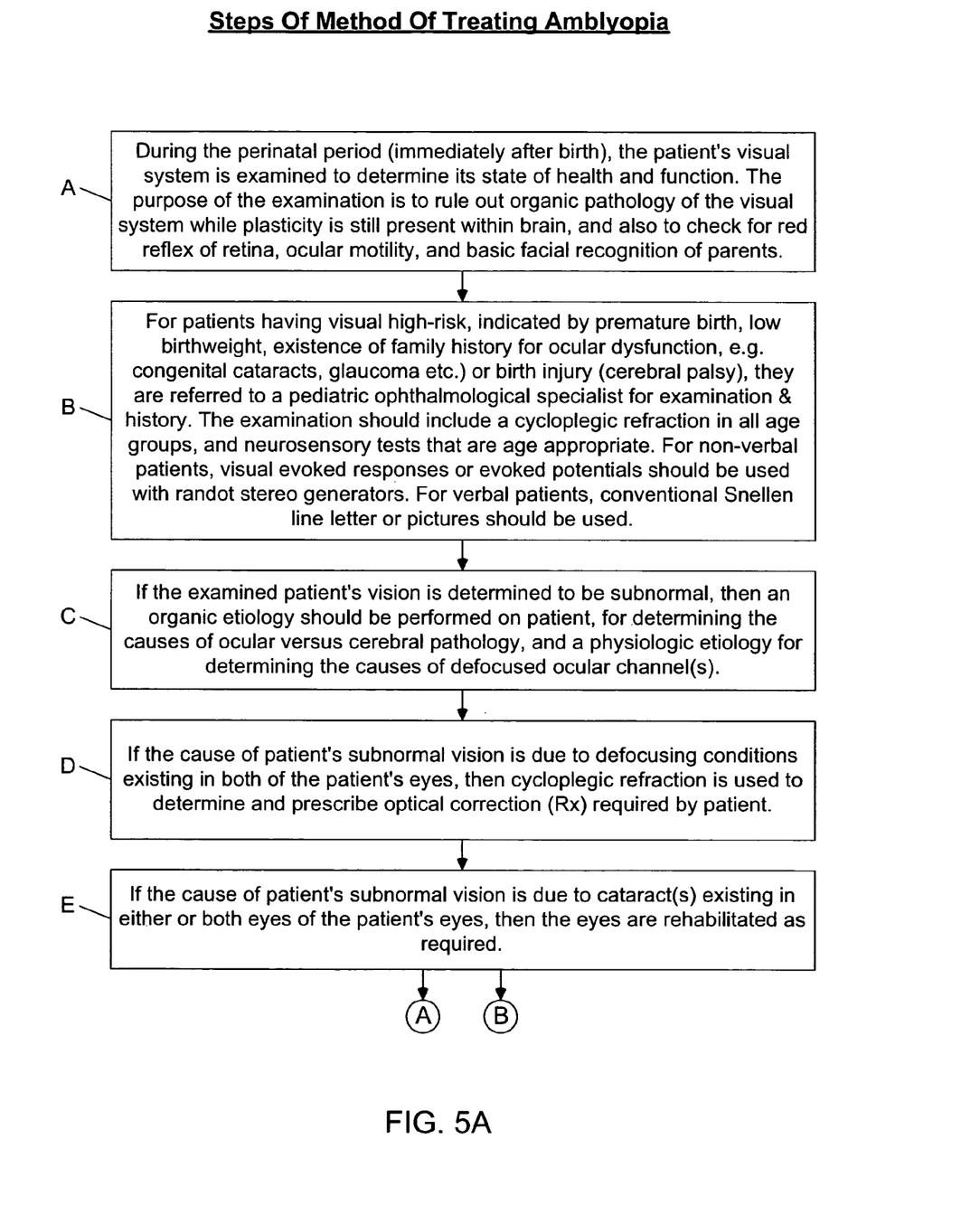
FIGS. 5A through 5D, taken together, set forth the steps associated with the preferred embodiment of the method of diagnosing and treating amblyopia in accordance with the principles of the present invention.
Figure 5B:
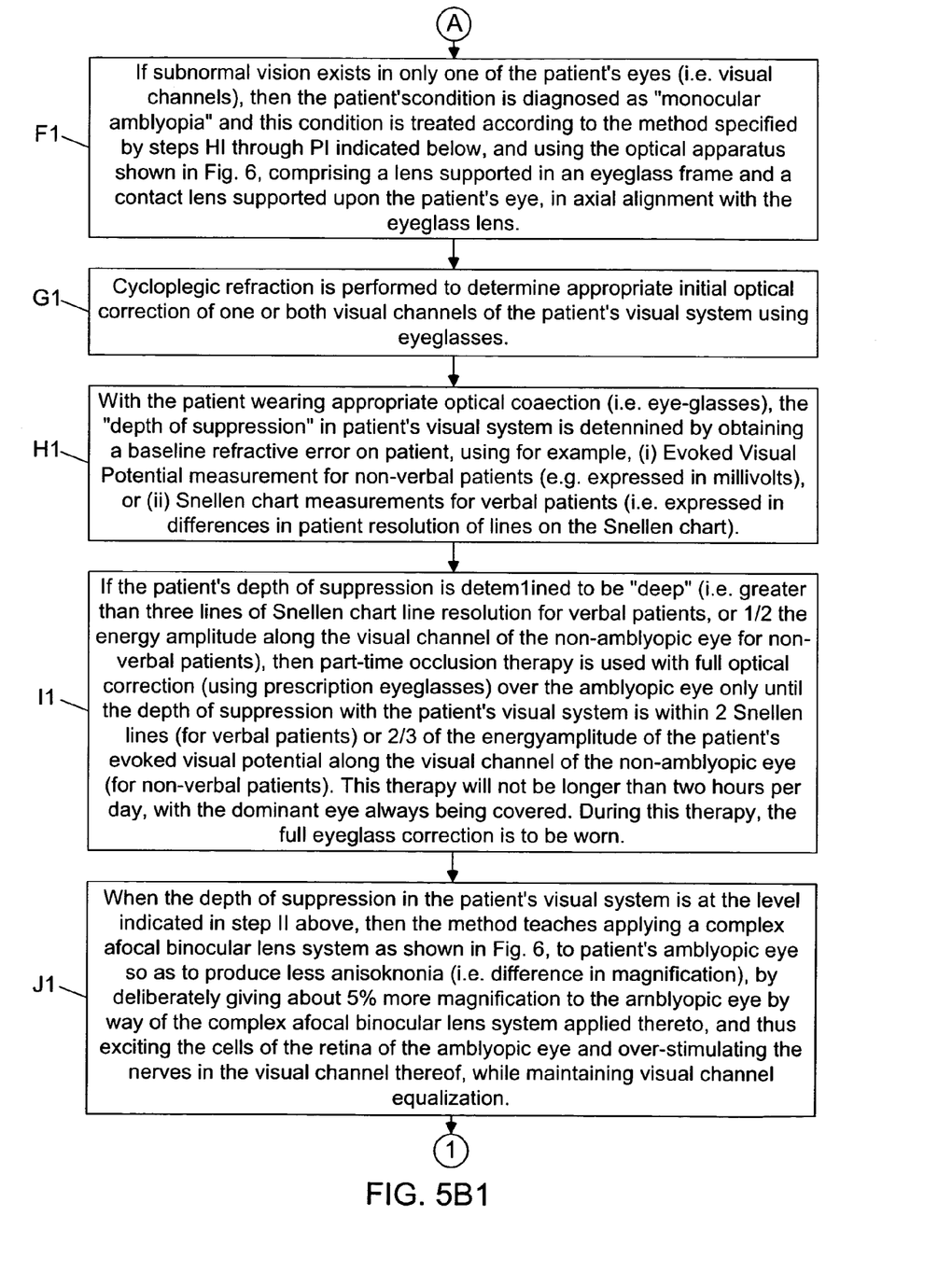
Figure 5B:
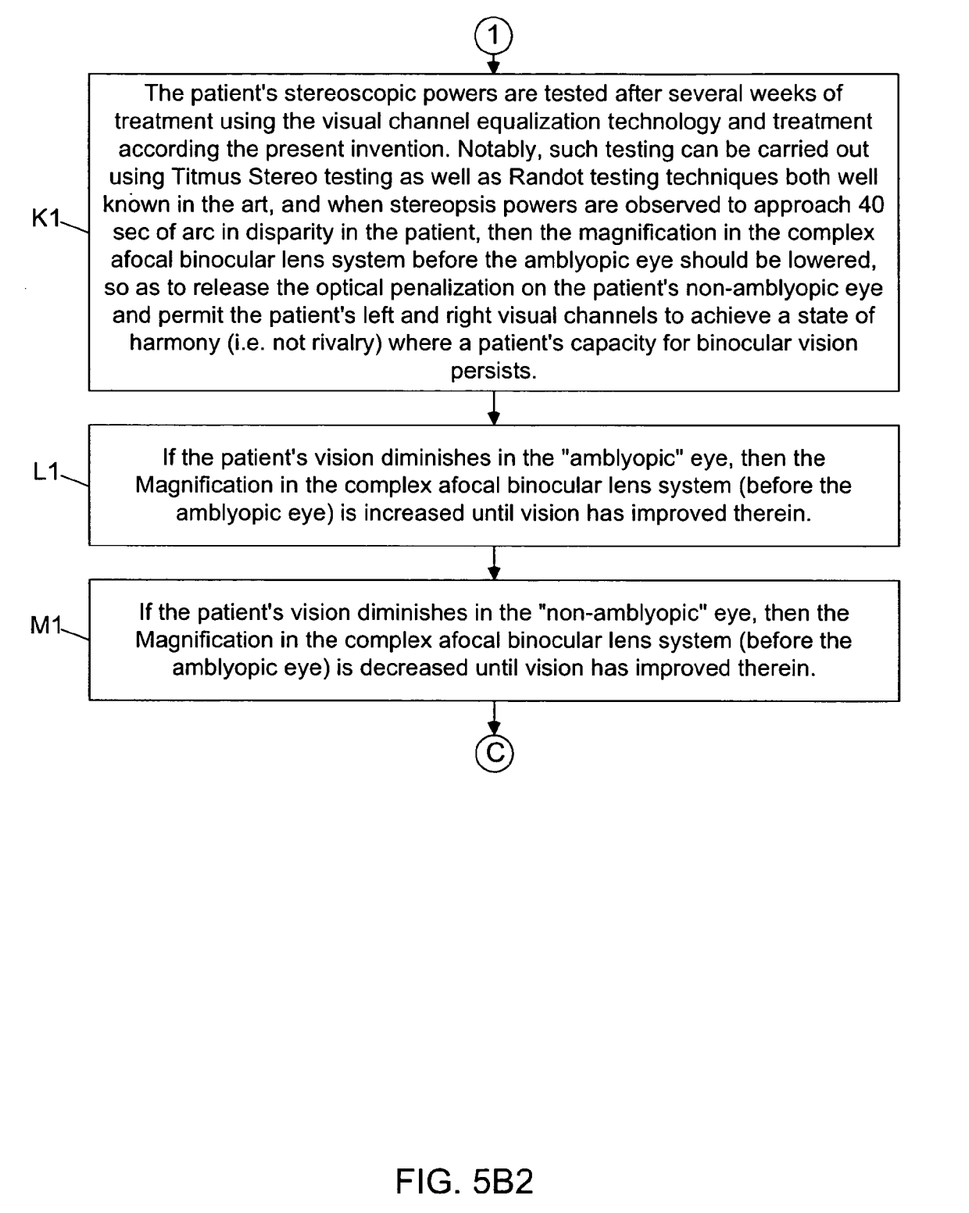

As indicated at Block A in FIG. 5A, the method teaches, during perinatal period (immediately after birth), examining the patient's visual system to determine state of health and function. The purpose of the examination is to rule out organic pathology of visual system while plasticity is still present within brain, and also to check for red reflex of retina, ocular motility, and basic facial recognition of parents.

As indicated at Block B in FIG. 5A, for patients having visual high-risk (indicated by premature birth, low birth-weight, existence of family history for ocular dysfunction, e.g. congenital cataracts, glaucoma etc.) or birth injury (cerbral palsy), the method teaches referring the patient to a pediatric ophthalmological specialist for examination & history. The examination should include a cycloplegic refraction in all age groups, and neurosensory tests that are age appropriate. For non-verbal patients, visual evoked responses or evoked potentials should be used with randot stereo generators. For verbal patients, conventional Snellen line letter or pictures should be used.

As indicated at Block C in FIG. 5A, if examined patient's vision is determined to be subnormal, then the method teaches performing an organic etiology on patient: for determining the causes of ocular versus cerbral pathology, and a physiologic etiology for determining the causes of defocused ocular channel(s).

As indicated at Block D in FIG. 5A, if the cause of patient's subnormal vision is due to defocusing conditions existing in both of the patient's eyes, then the method teaches prescribing optical correction (rx)—using cycloplegic refraction to determine optical correction required by patient.

Figure 6:
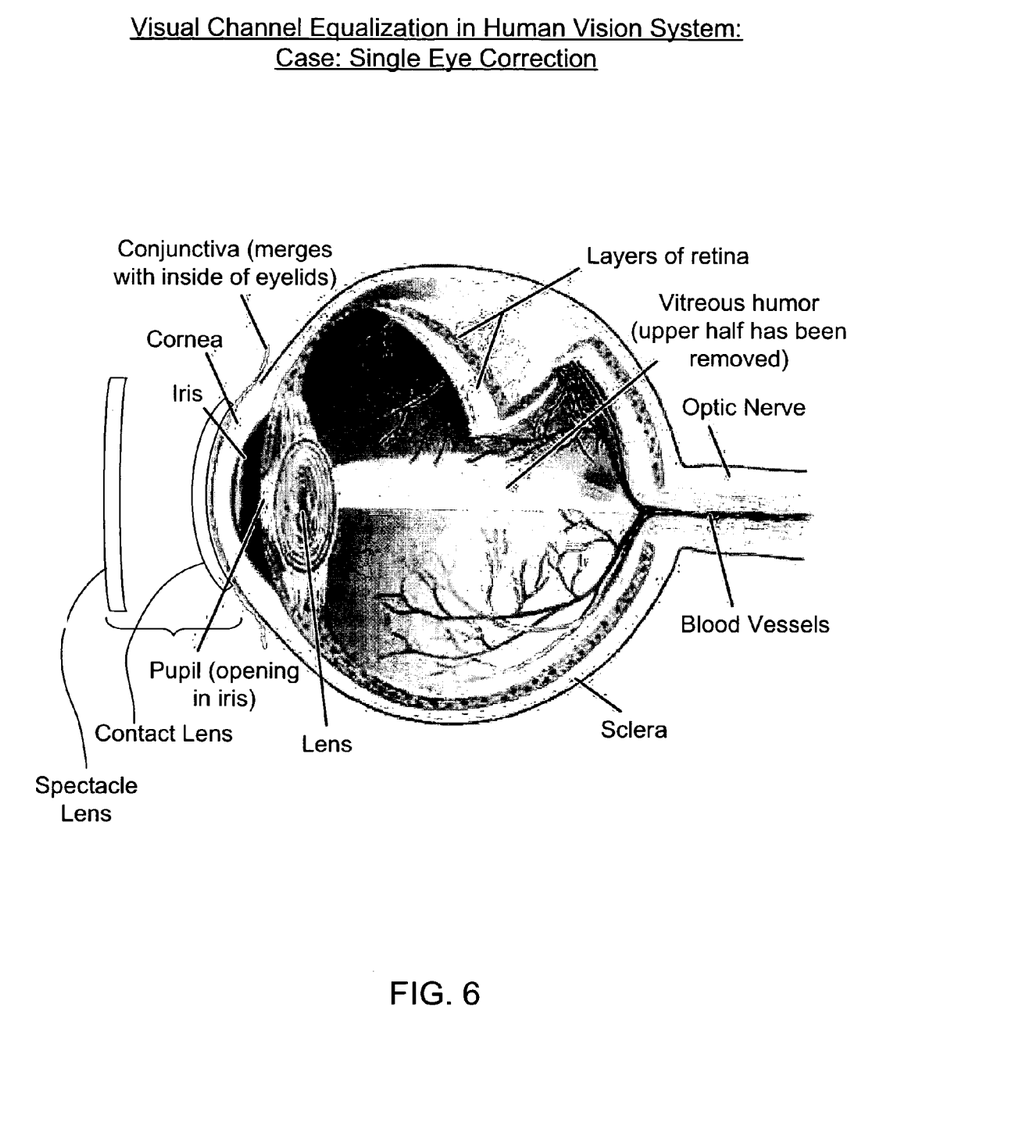
FIG. 6 is a schematic illustration showing a single eye in the human visual system, provided with a single afocal optical system (i.e. Galilean Optical System) for achieving visual equalization in a patient's human visual system afflicted by amblyopia.

As indicated at Block E in FIG. 5A, if the cause of patient's subnormal vision is due to cataract(s) existing in either or both eyes of the patient's eyes, then the method teaches rehabilitating the eyes as required Case of "Monocular Ambylopia" Diagnosis As indicated at Block Fi in FIG. 5B, if subnormal vision exists in only one of the patient's eyes (i.e. visual channel of his/her visual system), then the method teaches diagnosing the patient's condition as "monocular amblyopia" and treat according to the method specified by steps H1 through P1 indicated below, and using the optical apparatus shown in FIG. 6.

As indicated at Block G1 in FIG. 5B, the method teaches performing cycloplegic refraction to determine appropriate initial optical correction of one or both visual channels of patient's visual system.

As indicated at Block H1 in FIG. 5B, with patient wearing appropriate optical correction, the method teaches determining the "depth of suppression" in patient's visual system— by obtaining a baseline refractive error on patient:

(i) using visual evoked potential measurement for non-verbal patients (i.e. expressed in evps); and (ii) using Snellen chart measurements for verbal patients (i.e. expressed in differences in patient resolution of lines on the Snellen chart).

As indicated at Block I1 in FIG. 5B, if the patient's depth of suppression is determined to be "deep" (i.e. greater than three lines of Snellen chart line resolution for verbal patients, or ½ the energy amplitude along the visual channel of the non-amblyopic eye for non-verbal patients), then the method teaches using part-time occlusion therapy with full optical correction over the amblyopic eye until the depth of suppression with the patient's visual system is within 2 Snellen lines (for verbal patients) or ⅔ of the energy-amplitude of the patient's evoked visual potential along the visual channel of the non-amblyopic eye (for non-verbal patients). This therapy will not be longer than two hours per day, the dominant eye always being covered. During this therapy, the full glass correction is to be worn.

As indicated at Block J1 in FIG. 5B, when the depth of suppression in the patient's visual system is at the level indicated in step i above, then the method teaches applying a complex afocal binocular lens system to patient's amblyopic eye so as to produce less anisoknonia (i.e. difference in magnification), by deliberately giving about 5% more magnification to the amblyopic eye by way of the complex afocal binocular lens system applied thereto, and thus exciting the cells of the retina of the amblyopic eye and over-stimulating the nerves in the visual channel thereof. Magnification M is provided by the following formula:

Magnification %=$M$=($D$)×$t$/$n$:

wherein $D$=diopters of front surface power;

$t$=thickness in cm; and $n$=index of refraction of the plastic.

To insure contrast equality, pupil size is observed and the optical zone drapes

As indicated at Block K1 in FIG. 5B, the method teaches testing the patient's stereoscopic powers after several weeks of treatment (using Titmus Stereo testing as well as Randot testing), and when steropsis in the patient approaches 40 sec of arc in disparity, then lower the magnification in the complex afocal binocular lens system before the amblyopic eye, so as to release the optical penalization on the patient's non-amblyopic eye and approach harmony (i.e. not rivalry) between the patient's left and right visual channels. Care must exercised with such optical treatment of the amblyopic eye because prolonged over-stimulation of the nerves along the visual channel thereof induce amblyopia in the formerly non-amblyopic, undesirably causing reverse penalization of formerly non-amblyopic eye.

As indicated at Block L1 in FIG. 5B, if the patient's vision diminishes in the "amblyopic" eye, then the method teaches increasing the magnification in the complex afocal binocular lens system (before the amblyopic eye) then until vision has improved therein.

As indicated at Block M1 in FIG. 5B, if the patient's vision diminishes in the "non-amblyopic" eye, then the method teaches decreasing the magnification in the complex afocal binocular lens system (before the amblyopic eye) until vision has improved therein.

Figure 5C:
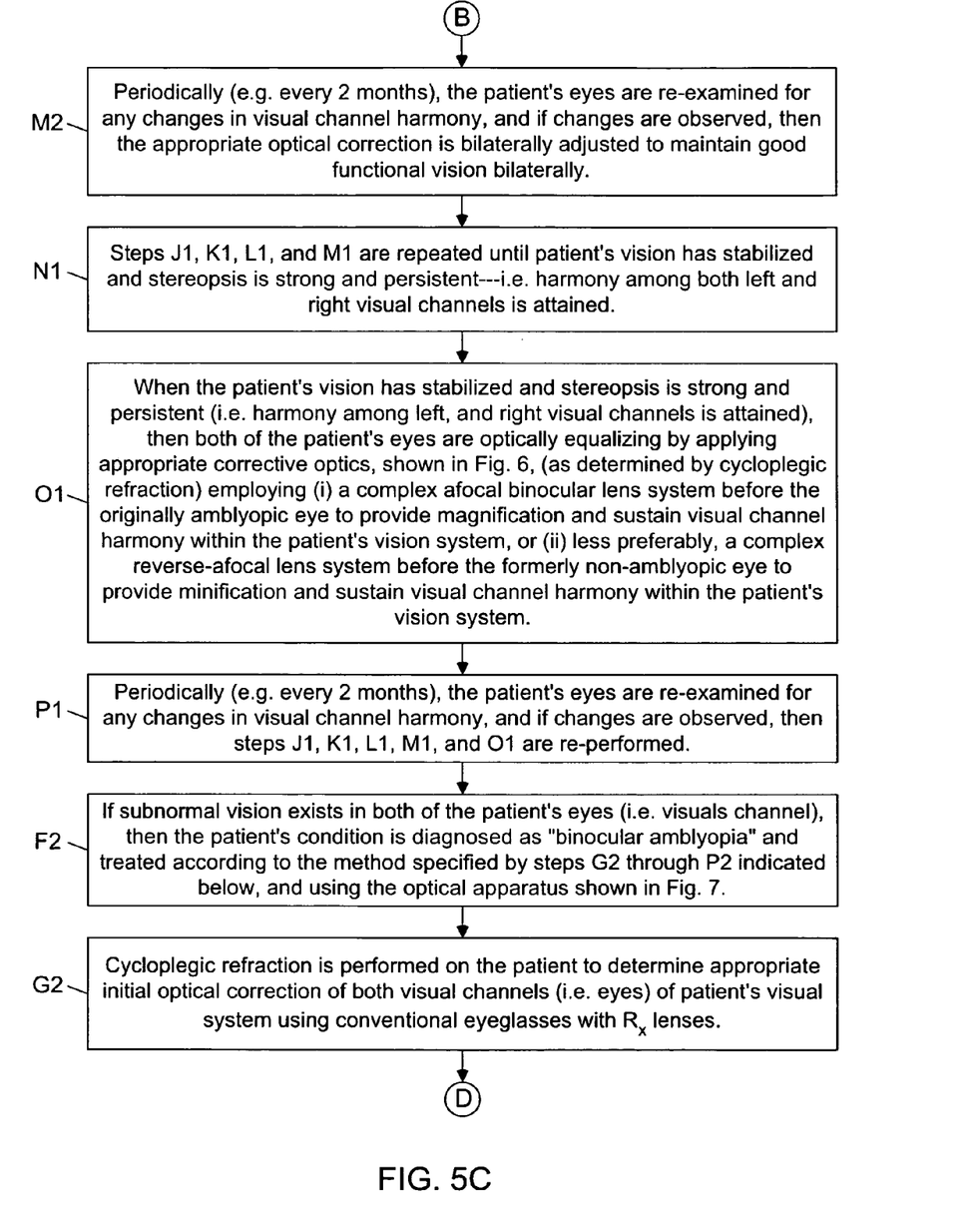
Figure 5D:
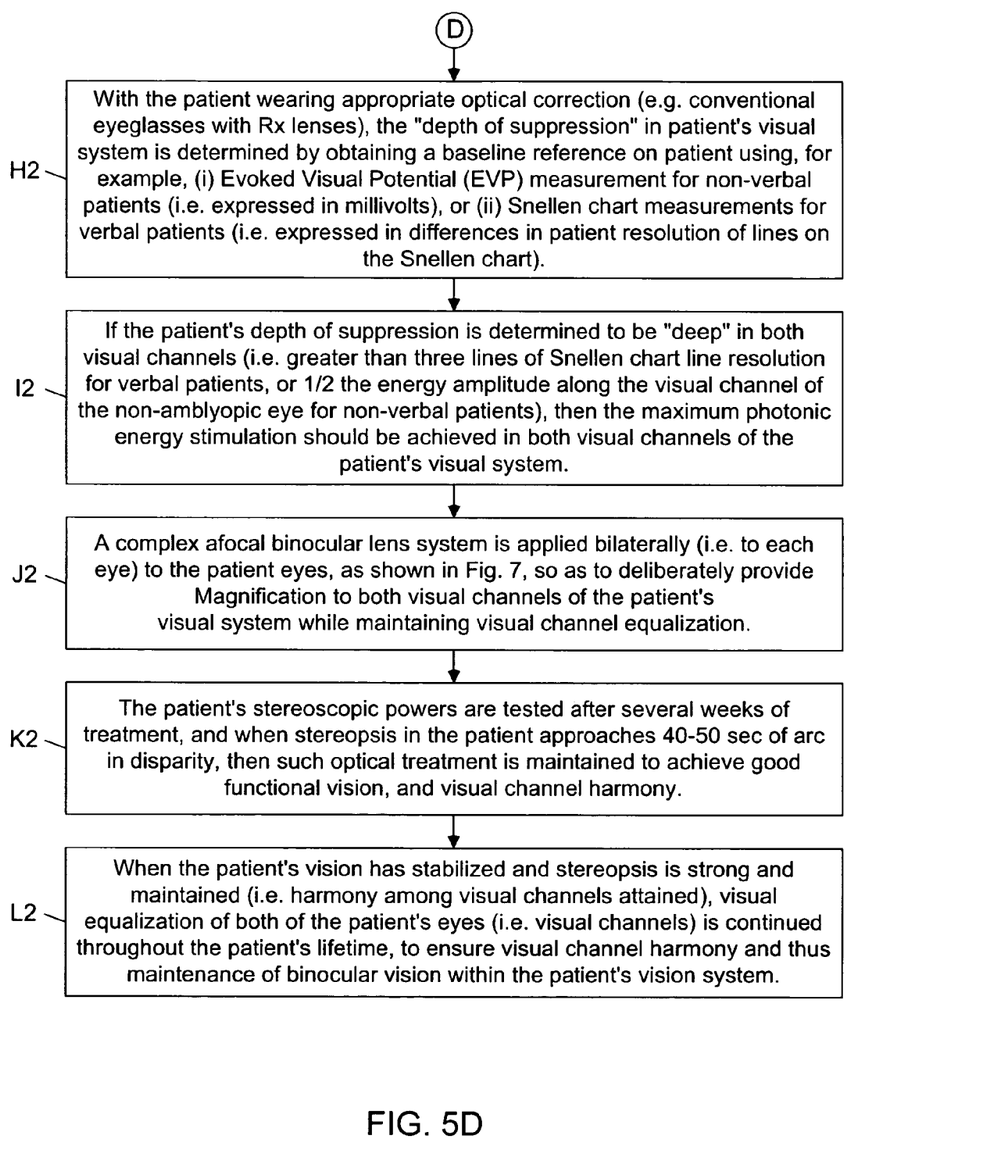

As indicated at Block N1 in FIG. 5C, the method then involves repeating Steps J1, K1 L1 and M1 until patient's vision has stabilized and steropsis is strong and persistent—i.e. harmony among visual channels attained.

As indicated at Block O1 in FIG. 5C, when the patient's vision has stabilized and steropsis is strong and persistent (i.e. harmony among visual channels attained), then the method teaches optically equalizing both of the patient's eyes by applying appropriate corrective optics (determined by cycloplegic refraction) employing (i) a complex afocal binocular lens system before the originally amblyopic eye to provide magnification and sustain visual channel harmony, or (ii) less preferably, a complex reverse-afocal lens system before the formerly non-amblyopic eye to provide minification and sustain visual channel harmony.

As indicated at Block P1 in FIG. 5C, periodically (e.g. every 2 months), the method teaches re-examining the patient's eyes for any changes in visual channel harmony, and if changes are observed, then re-perform steps J1, K1, L1 M1 and O1.

Case of "Binocular Ambylopia" Diagnosis

Figure 7:
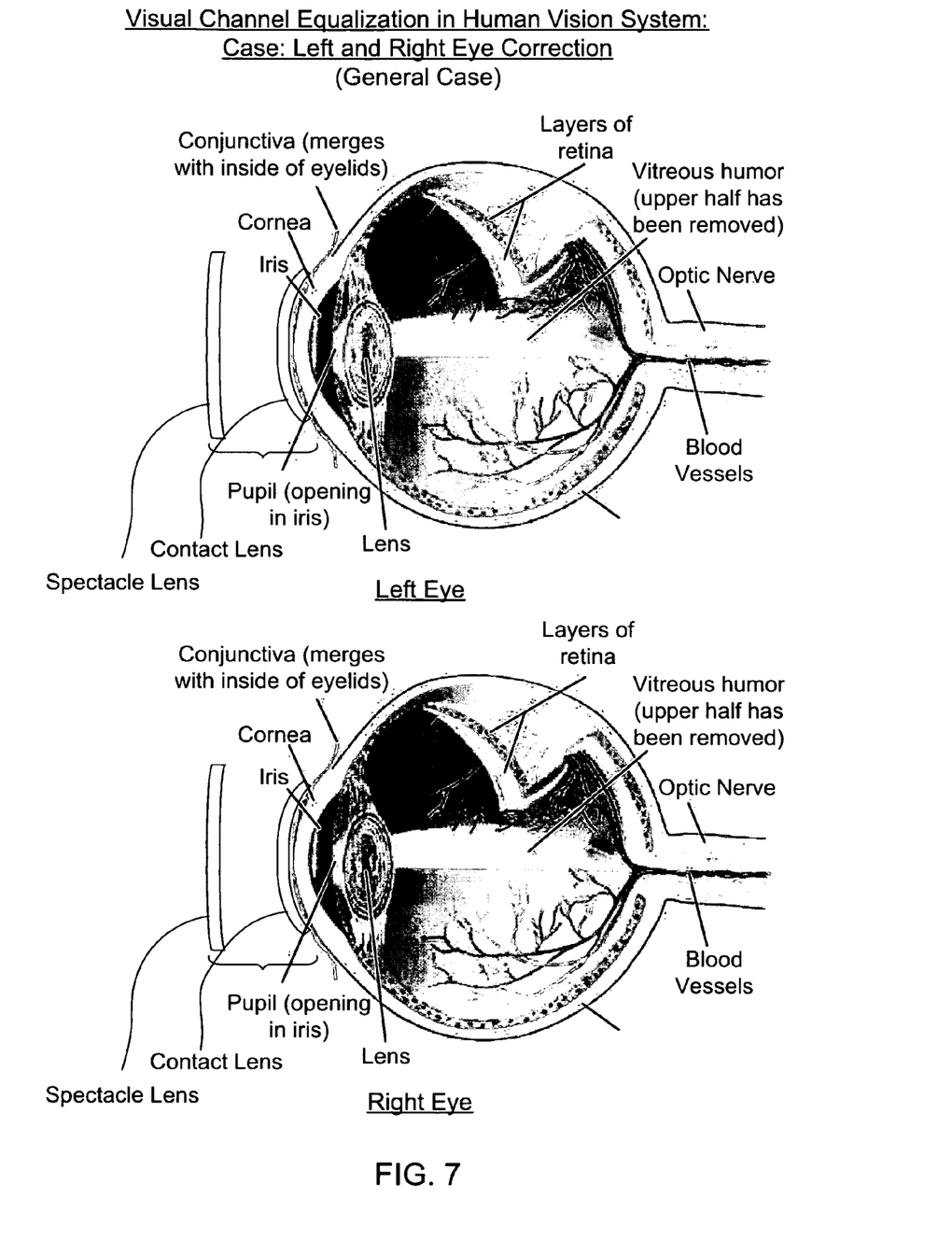
FIG. 7 is a schematic illustration showing both eyes in the human visual system, each being provided with an afocal optical system (i.e. Galilean Optical System) for achieving visual equalization in a patient's human visual system afflicted by amblyopia.

As indicated at Block F2 in FIG. 5C, if subnormal vision exists in both of the patient's eyes (i.e. visuals channel), then the method teaches diagnosing the patient's condition as "binocular amblyopia" and treat according to the method specified by steps g2 through p2 indicated below, and using the optical apparatus shown in FIG. 7.

As indicated at Block G2 in FIG. 5C, the method teaches performing cycloplegic refraction to determine appropriate initial optical correction of both visual channels (i.e. eyes) of patient's visual system As indicated at Block H2 in FIG. 5B, with patient wearing appropriate optical correction, the method teaches determining the "depth of suppression" in patient's visual system—by obtaining a baseline reference on patient:

(i) using visual evoked potential (EVP) measurement for non-verbal patients (i.e. expressed in millivolts)

(ii) using Snellen chart measurements for verbal patients (i.e. expressed in differences in patient resolution of lines on the Snellen chart) As indicated at Block I2 in FIG. 5C, if the patient's depth of suppression is determined to be "deep" in both visual channels (i.e. greater than three lines of snellen chart line resolution for verbal patients, or ½ the energy amplitude along the visual channel of the non-amblyopic eye for non-verbal patients), then the method teaches achieving maximum photonic energy stimulation in both visual channels of the patient's visual system.

As indicated at Block J2 in FIG. 5C, the method teaches applying bilaterally (i.e. to each eye) complex afocal binocular lens system to the patient eyes so as to deliberately provide magnification to both visual channels of the patient's visual system.

As indicated at Block K2 in FIG. 5C, the method teaches testing the patient's stereoscopic powers after several weeks of treatment, and when steropsis in the patient approaches 40–50 sec of arc in disparity, then maintaining such optical treatment to achieve good functional vision, and visual channel harmony.

As indicated at Block L2 in FIG. 5C, when the patient's vision has stabilized and steropsis is strong and maintained (i.e. harmony among visual channels attained), the method teaches continuing optical equalization of both of the patient's eyes throughout the patient's lifetime.

As indicated at Block M2 in FIG. 5C, periodically (e.g. every 2 months), the method teaches re-examining the patient's eyes for any changes in visual channel harmony, and if changes are observed, then bilatarally adjusting the appropriate optical correction to maintain good functional vision bilaterally.

Figure 8:
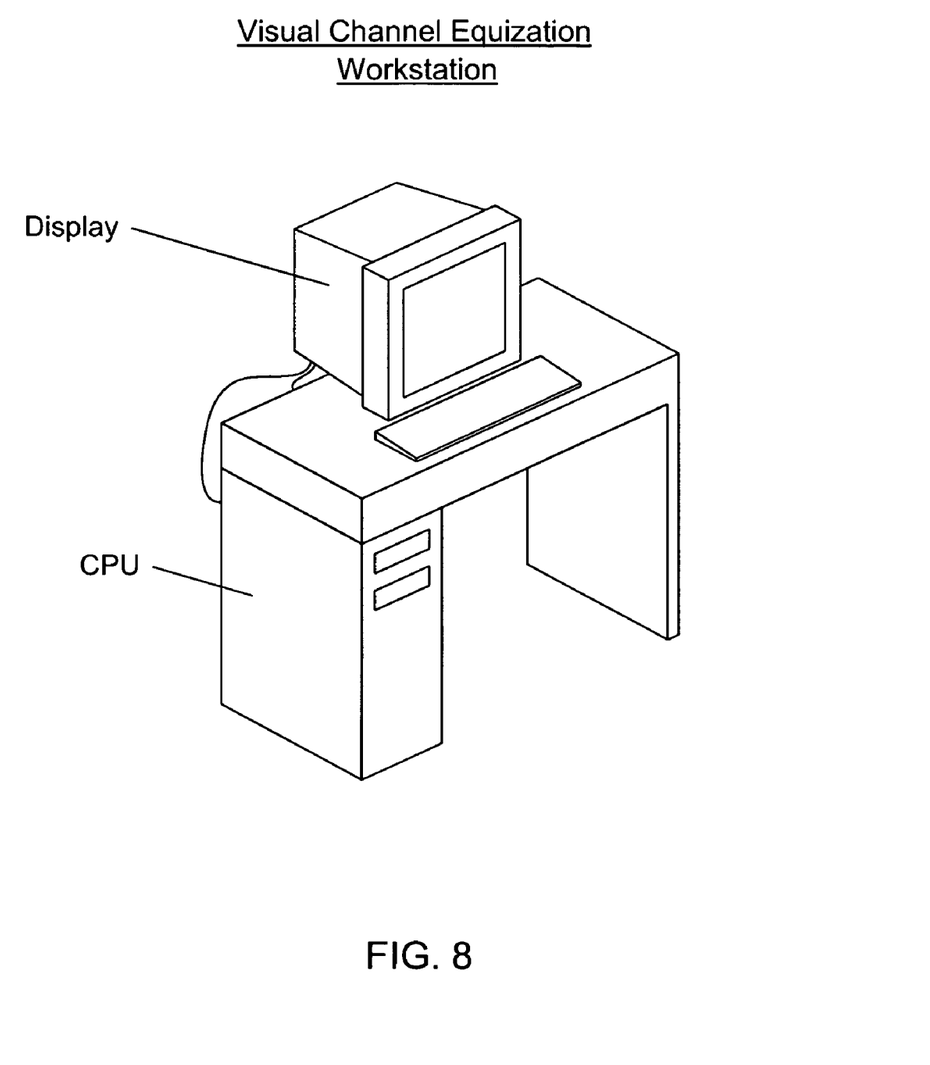
FIG. 8 is a perspective view of a computer-based Visual-Channel Equalization Management Workstation that is equipped with computer programs written to carry out the method of amblyopia treatment in accordance with the present invention.
Figure 9:
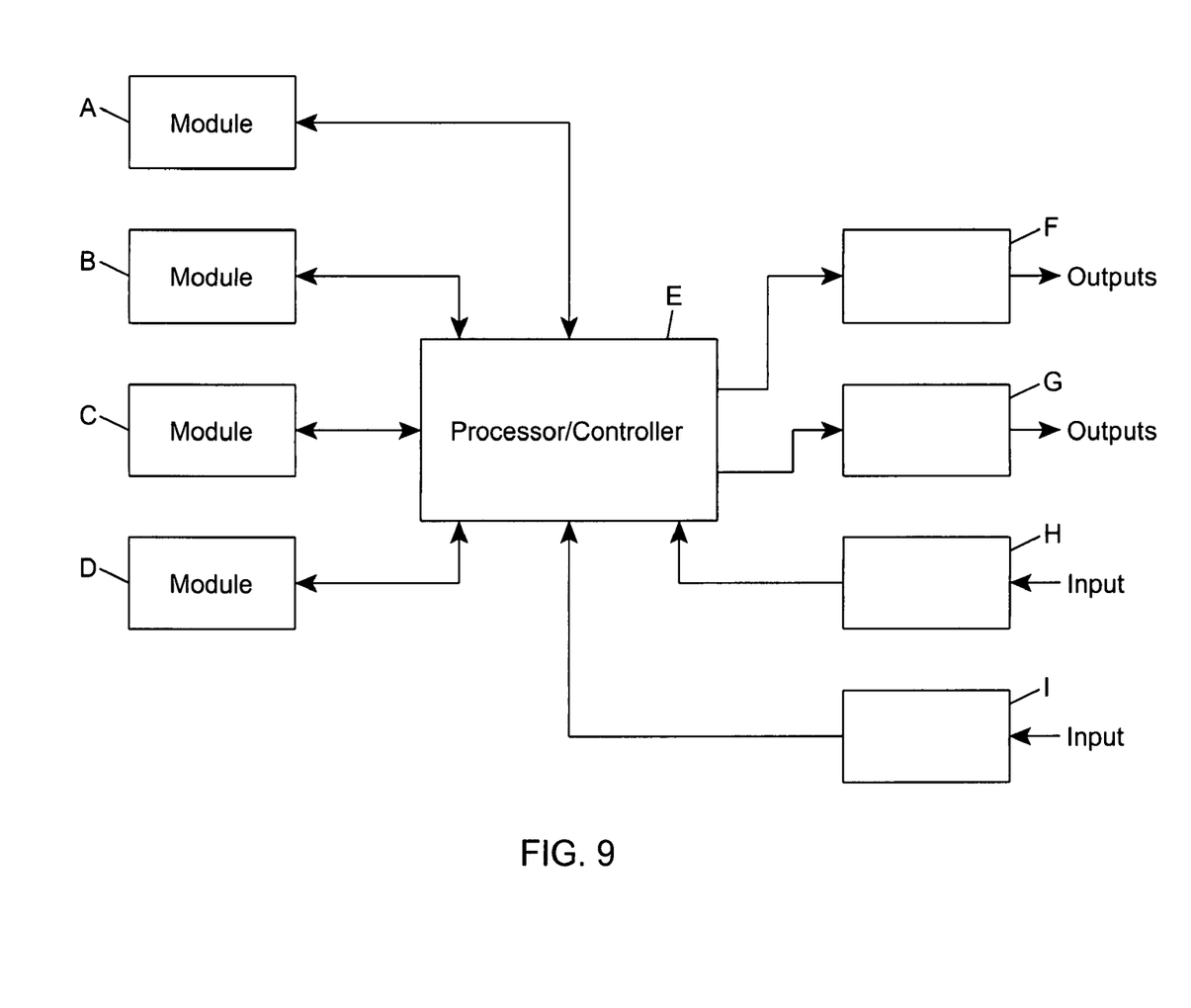
FIG. 9 is a system block diagram illustrating the various software-based modules used in the computer-based Visual-Channel Equalization Management Workstation shown in FIG. 8, in order to carry out the method of amblyopia treatment in accordance with the present invention.

In FIG. 8, a computer based workstation is shown for carrying out and managing the method of diagnosis and treatment of the present invention, generally comprises a CPU, expandable memory volume, LCD panel, keyboard and input devices as CCD-based slit lamps, keratometers, contrast threshold charts, evoked visual potential (EVP) sine wave and square wave generators and the like As shown in FIG. 9, the software program designed to carry out and manage the method comprises a number of software modules, namely: a patient information management module A; a left visual channel modeling module for managing information models relating to the structure and function of the optical components in the patient's left visual channel B; a right visual channel modeling module for managing information models relating to the structure and function of the optical components in the patient's right visual channel C; a visual system performance metric modeling module D; and other supporting modules E and F, required to carry out the efficient practice of the method hereof in a clinical setting found in doctor offices, hospitals, clinics and the like.

It is understood that the method and apparatus of the illustrative embodiments may be modified in a variety of ways which will become readily apparent to those skilled in the art, and having the benefit of the novel teachings disclosed herein. All such modifications and variations of the illustrative embodiments thereof shall be deemed to be within the scope and spirit of the present invention as defined by the accompanying Claims to Invention.

What is claimed is:

1. A method of treating monocular amblyopic conditions within a patient's human vision system having left and right visual channels so that persistent binocular vision is achieved, said method comprising the steps:
   (a) applying a complex afocal binocular lens system to an amblyopic eye of a patient, including a contact lens on the amblyopic eye, to provide the amblyopic eye with more magnification than the non-amblyopic eye during treatment so as to over-stimulate the neural pathways along the visual channel of the amblyopic eye, without applying occlusion therapy or penalization therapy along the visual channel not afflicted by amblyopia; and
   (b) during the course of treatment, testing the powers of the patient's human vision system including the patient's power of stereoscopic vision and adjusting the optical correction provided by said complex afocal binocular lens system to enable good functional vision bilaterally; and
   (c) when, during the course of treatment, the stereoscopic power of the patient's human vision system approaches a predetermined amount of disparity, then adjusting the magnification in said complex afocal binocular lens system before the amblyopic eye, so as to enable a state of harmony to be attained between said left and right visual channels of the patient's human vision system, at which a state of persistent binocular vision is achieved in the patient.

2. The method of claim 1, which further comprises during step (b), if the power of the patient's human vision system diminishes in the amblyopic eye, then increase the magnification in said complex afocal binocular lens system before the amblyopic eye until the power of the patient's human vision system has improved.

3. The method of claim 1, which further comprises during step (b), if the power of the patient's human vision system diminishes in the non-amblyopic eye, then decrease the magnification in said complex afocal binocular lens system before the amblyopic eye until the power of the patient's human vision system has improved.

4. The method of claim 1, which further comprises repeating steps (b) and (c) during the course of treatment until the patient's vision has stabilized and harmony among the left and right channels is attained, evidenced by strong and persistent stereoscopic powers of vision in the patient's human vision system.

5. A method of treating binocular amblyopic conditions within a patient's human vision system having left and right visual channels so that persistent binocular vision is achieved, said method comprising the steps:
   (a) applying pair of reverse-afocal binocular lens systems before a pair of amblyopic eyes in a patient so as to treat binocular amblyopia, including applying a contact lens on each amblyopic eye to provide the more amblyopic eye with magnification and the less amblyopic eye with minification during treatment so as to over-stimulate the neural pathways along the visual channel of more amblyopic eye and under-stimulate the neural pathways along the visual channel of the less amblyopic eye, in comparison to the more amblyopic eye; and
   (b) during the course of treatment, testing the powers of the patient's human vision system, including the patient's power of stereoscopic vision, and adjusting the optical correction provided by said pair of reverse-afocal binocular lens systems to enable good functional vision bilaterally; and
   (c) when the patient's power of stereoscopic vision approaches a predetermined amount of disparity, then adjusting the magnification and minification in said pair of reverse-afocal binocular lens systems before the patient's eyes, so as to enable a state of harmony to be attained between said left and right visual channels of the patient's human vision system, at which a state of persistent binocular vision is achieved in the patient.

6. The method of claim 5, which further comprises repeating steps (b) and (c) so as to re-examine the patient's eyes for any changes in visual channel harmony, and if changes are observed, then bilaterally adjusting the optical correction provided by said pair of reverse-afocal binocular lens systems so as to maintain good functional vision bilaterally, and the patient's power of stereoscopic vision.

* * * * *